US006953437B1

(12) United States Patent
Reiffel

(10) Patent No.: US 6,953,437 B1
(45) Date of Patent: Oct. 11, 2005

(54) THERMOMETER IMPLANTS

(76) Inventor: Leonard Reiffel, 602 Deming Pl., Chicago, IL (US) 60614

(*) Notice: Subject to any disclaimer, the term of this patent is extended or adjusted under 35 U.S.C. 154(b) by 0 days.

(21) Appl. No.: 10/018,713

(22) PCT Filed: Jul. 2, 1999

(86) PCT No.: PCT/US99/15036

§ 371 (c)(1),
(2), (4) Date: Dec. 12, 2001

(87) PCT Pub. No.: WO01/01850

PCT Pub. Date: Jan. 11, 2001

(51) Int. Cl.$^7$ .......................... A61B 5/01; G01K 5/02
(52) U.S. Cl. .......................... 600/549; 374/201
(58) Field of Search .......................... 600/549; 374/100, 374/187, 201, 137, 120, 190

(56) References Cited

U.S. PATENT DOCUMENTS 3,893,111 A * 7/1975 Cotter .......................... 600/549
4,036,060 A * 7/1977 Deficis .......................... 374/201
4,138,998 A 2/1979 Nowogrodzki
4,170,138 A 10/1979 Wiebe
4,176,551 A * 12/1979 Hammer et al. .......... 374/161
5,109,853 A 5/1992 Taicher et al.
5,446,452 A * 8/1995 Litton .......................... 600/549
5,902,251 A * 5/1999 vanHooydonk .......... 600/549
6,250,800 B1 * 6/2001 Reiffel .......................... 374/190

* cited by examiner

*Primary Examiner*—Eric F. Winakur
(74) *Attorney, Agent, or Firm*—Hallihan Intellectual Property Law

(57) ABSTRACT

A thermometer implant (10), especially useful in medical diagnostic and therapeutic procedures, comprises a thermometer body (15) containing a fluid (13) which expands, and contracts to a fluid length (14) that indicates a target temperature at a target time, and which is located in a body from where the expanding fluid is not visible at the target time, with the fluid length (14) at the target time being measured outside the body.

13 Claims, 1 Drawing Sheet

15
71
11
13
14
71
12

15
71
11
13
14
71
12

15a
11a
11'a
13a
14a
12a 15b
11b 13b
14b
133
132
131
134
12b
111
122
122
123
121
112

312
371
311

316
214
216
211
271
212
15c

THERMOMETER IMPLANTS

BACKGROUND OF THE INVENTION

A thermometer implant—especially useful in medical diagnostic and therapeutic procedures—comprises a thermometer body containing a fluid which expands and contracts to a fluid length which indicates a target temperature at a target time and which is located in a body from where the fluid length is not visible at the target time, with the fluid length at the target time being measured outside the body.

When, for example, a cancerous tumor is treated by hyperthermia or cryotherapy it is very important to control the temperature in the tumor as well as the temperature in healthy tissue. Since existing temperature sensors are not adequate to the task, workers have long been seeking new ways to measure the temperature for such cases.

An implanted reflector which reflects a microwave signal as a function of temperature is shown by Nowogrodzki in U.S. Pat. No. 4,138,998. An implanted element which has temperature dependent nuclear magnetic resonance properties is shown by Taicher in U.S. Pat. No. 5,109,853.

The invention shown here is based on the discovery that small, expanding fluid thermometers can be made with properties which solve this long outstanding problem.

SUMMARY OF TE INVENTION

One form of this invention of thermometer implants comprises a thermometer body, the thermometer body enclosing a channel and a bulb, the channel being terminated by the bulb at one end, the channel and the bulb containing a fluid, the fluid expanding and contracting along the channel to a fluid length which is functionally related to a target temperature of the bulb at a target time, the thermometer body being located in a subject body from where the fluid length is not visible at the target time, and thermometer body properties and fluid properties together making possible measurement of the fluid length outside of the subject body.

Alternative forms and objects of the invention will be comprehended in the drawings and description, which will make additional equivalent forms and objects obvious hereafter to persons skilled in the art.

DESCRIPTION OF THE PREFERRED EMBODIMENTS

Figure 1:
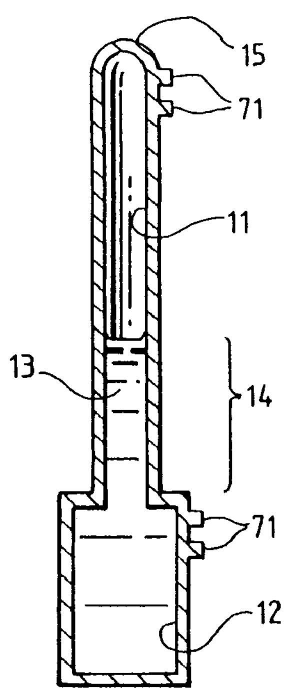
FIG. 1 shows a cross section of a basic form of a thermometer implant.

A cross section of a basic form 10 of a thermometer implant is shown in FIG. 1. This basic form comprises a thermometer body 15 which encloses a channel 11 terminated at one end by a bulb 12 with a fluid 13 contained in the bulb and the channel. As the temperature of the bulb increases and decreases the fluid 13 expands and contracts along the channel to a fluid length 14 which is functionally related to a target temperature of the bulb at a target time.

The target time is a time when temperature data is desired, and the target temperature is the temperature of the bulb at the target time.

Dimensions of an example thermometer implant which can be implanted in living tissue—for example by using standard biopsy techniques—are: length of thermometer 20 mm; channel inside diameter 50 microns; bulb length 5 mm; bulb inside diameter 0.75 mm; bulb outside diameter 1.25 mm; thermometer outside diameter away from bulb 90 microns. A suitable fluid in a thermometer with these dimensions will expand along the channel at about 1 mm per degree Celsius. Thus, for example, if an accuracy of 0.3 Celsius degrees is required, then the fluid length must be measured to an accuracy of 0.3 mm. This sensitivity is that sought in hyperthermia treatments of cancerous tumors. Smaller and larger thermometers can be made as needed for specific applications with more or less stringent requirements for size and sensitivity.

The invention is also adapted to cases where thermometers are located in a subject body which is not living tissue. However, when the subject body is in, and alternatively intended for use in, a living human, this necessarily means that the properties of the thermometer body and the properties of the fluid must meet standards set forth in prevailing regulations. In the United States these would be the regulations of the U.S. Food and Drug Administration. In other countries these would be regulations of the corresponding agency.

The thermometer body is located in a subject body from where the fluid length is not visible at the target time. This means that at the target time the fluid length can not be measured, to an accuracy required by an application such as that described above, using visible light. This meaning excludes the common case where a thermometer is removed from a body and the fluid length is then measured, because in this common case the fluid will expand and contract as the temperature of the bulb changes outside of the subject body and the fluid length will indicate the temperature of the bulb outside of the subject body at a time later than the target time.

Thus, the fluid length at the target time must be measured outside of the subject body, for example by projecting an image of the fluid length outside of the body at the target time. Thermometer body properties and fluid properties which together make possible measurement of the fluid length outside of the body and apparatus which is used to project an image of the fluid length outside of a subject body and is used to measure the image of the fluid length along with methods to calibrate this measurement are specified in the copending international patent application PCT/US98/27316 which is incorporated herein by reference.

Thermometer body properties and fluid properties can be chosen together to match the method and apparatus used to measure the fluid length outside of the subject body. For example, in the case of the x-ray method and apparatus shown in the above reference, resorbable lactide polymers, for example, could provide the needed thermometer body properties as could many other substances, and Iohexol, an x-ray contrast agent, for example could provide the needed properties for the fluid as could many other substances.

Figure 2:
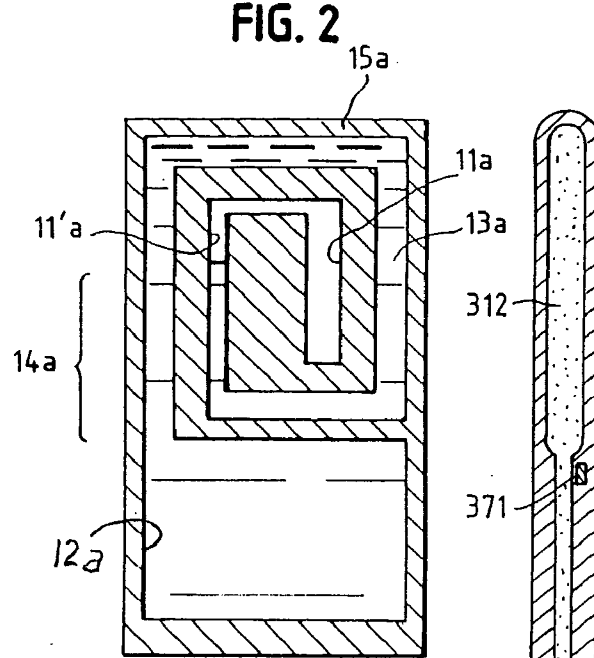
FIG. 2 shows a cross section of an alternate form of a thermometer implant with the channel folded and with a varying channel area.

In FIG. 2 a cross section of an alternate form of thermometer implants is shown. Here the channel 11*a*, which is enclosed by a thermometer body 15*a* and which is terminated at one end by a bulb 12*a* with a fluid 13*a* contained in the bulb and the channel, is folded so that the length of the channel 13*a* is increased greatly with little increase in the overall size of the thermometer body. A spiral-like folding is shown, but other foldings such as helical foldings and bellows foldings can be used.

Figure 3:
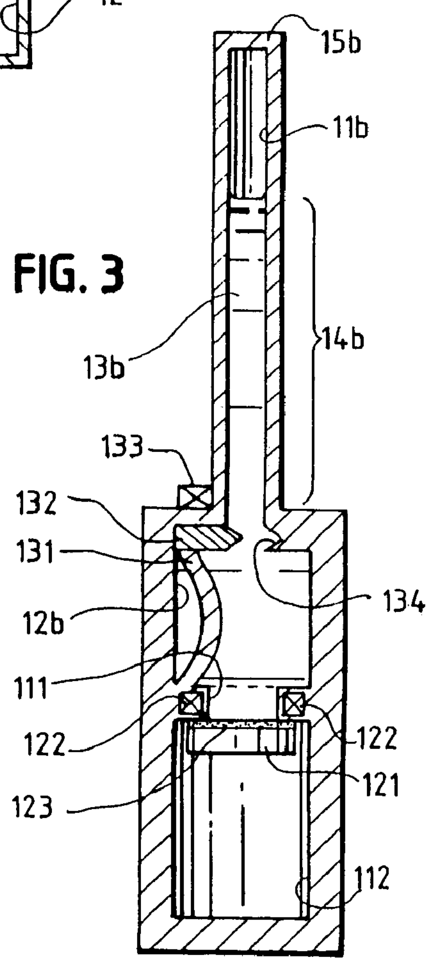
FIG. 3 shows a cross section of another alternate form of a thermometer implant with a trigger mechanism.

In FIG. 3 a form of a thermometer implant with a trigger mechanism is shown. This form is adapted to applications where the temperature of the bulb at a target time must be measured but where, at the target time, an image of the fluid length is not projected outside the body. When the trigger mechanism is activated at the target time, then the trigger mechanism locks the fluid in the channel at the fluid length which indicates the temperature of the bulb at the target time. This locked fluid length can be measured at a later time by projecting an image of the fluid length outside of the subject body. This triggered form of thermometer implants can also be removed from the subject body well after the fluid length has been locked and the fluid length then measured outside of the body, because the fluid length is still indicating the target temperature of the bulb inside of the subject body at the target time when the fluid length was locked.

In the triggered form the thermometer body 15*b* encloses a channel 11*b* terminated at one end by a bulb 12*b* with a fluid 13*b* contained in the bulb and the channel. In one form of a trigger mechanism the bulb also comprises an escape chamber 112 connected to the main chamber of the bulb by an escape channel 111 so that the fluid in the main chamber can escape to the escape chamber when a seal 121, which is sealed across the escape channel, is removed at a target time. When the fluid in the main chamber escapes, then the fluid in the channel 11*b* remains in place at a length indicating the temperature of the bulb when the seal 121 was removed.

One form of a remotely activated trigger mechanism comprises a magnet 122 around the escape channel 111 which holds a ferromagnetic seal 121 with a ferromagnetic liquid sealant 123 in place, and an external coil (not shown) which, when energized, demagnetizes the magnet 122 so that the seal 121 and the sealant 123 move away from the escape channel.

In some cases it is desirable to block the path between the channel and the bulb as the seal 121 is opened. One way to do this is to provide a channel seal 132 which is attached to the thermometer body by an arm 131 and which is held open by a channel magnet 133. When the channel magnet 133 is demagnetized by energizing the external coil, the arm 131, which is biased to move the channel seal across the channel, moves the channel seal 132 into a seat 134 thus closing the path between the channel and the bulb main chamber.

A first triggered thermometer implant can be triggered by a first demagnetizing external magnetic field without triggering a second thermometer implant which can be triggered later by a second, larger demagnetizing external magnetic field. Thus, each of several triggered thermometers can be triggered selectively at subsequent times by energizing the external coil to increasing magnetic fields at subsequent times.

Other forms for a trigger mechanism will be obvious hereafter by people skilled in the art. For example, adding the well known pinch region to the channel will yield a triggered maximum thermometer implant.

In FIG. 2 another variation which can be incorporated into any of the forms a thermometer implant is shown. Here there is a channel portion 11'*a* which has a smaller area than the remainder 11*b* of the channel. A varying area along the channel changes the sensitivity of the thermometer implant accordingly. Thus, this thermometer implant could have maximum sensitivity around a critical value of temperature and have less sensitivity at other temperatures.

Along with a thermometer implant at least one sequent thermometer implant can be located in the subject body. Each of these several thermometer implants can be distinguished from the others by its spatial position relative to the others. Also, each of several thermometer implants can be identified by the set of identifying markers.

A set of markers 71 is shown in FIG. 1 attached to the thermometer body at the bulb end of the thermometer body and at locations away from the bulb. Sets of markers comprising various combinations of markers can be used as identifying sets of markers in order to distinguish one thermometer body from a sequent thermometer body. A marker in a set can also be used as a gauge marker to calibrate a projected image of the fluid.

The markers shown are depicted as knobs, but various other marking means can be used such as enclosing markers in the thermometer body. The bulb 12 can be given various shapes which can be distinguished and this can comprise a set of markers which can take the place of the set 71 shown.

A sequent thermometer body encloses a sequent channel like 11 which is terminated at one end by a sequent bulb like 12. The sequent bulb and the sequent channel contain a sequent fluid like 13 which expands along the sequent channel to a sequent fluid length like 14 which is a function of a sequent target temperature of the sequent bulb at a sequent target time, where the sequent target time could be the same as the target time.

An alternative multi-component form of a thermometer implant which has at least the elements of the basic form of a thermometer implant, shown in FIG. 1, except that the set of markers may be left off, also encloses at least one sequent bulb and sequent channel containing a sequent fluid, with the sequent bulb being like 12, the sequent channel being like 11, and the sequent fluid being like 13 and expanding along the sequent channel to a fluid length like 14 functionally related to a sequent target temperature of the sequent bulb at a sequent target time which can be the same as the target time. When the multi-component thermometer is located in the subject body the several fluid lengths are measured outside of the body to determine the several temperatures of the bulbs.

Figure 4:
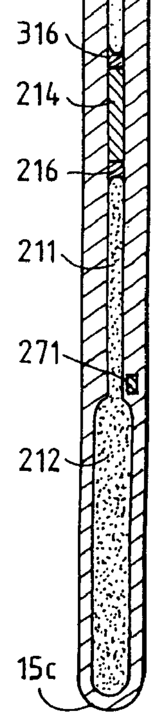
FIG. 4 shows a multi-component thermometer implant in a differential thermometer configuration.

A differential sub-form of the multi-component form of the thermometer implants shown in FIG. 4 is adapted to easily monitor variations in the temperature of abnormal tissue relative to adjacent healthy tissue. Here the thermometer body 15*c* encloses the bulb 212 terminating the channel 211 and encloses the sequent bulb 312 terminating the sequent channel 311, with the channel and the sequent channel together forming a contiguous channel.

A movable piston 214—which can be accompanied by sealant 216 and 316—rides in this contiguous channel dividing the expansion and contraction of the fluid from the expansion and contraction of the sequent fluid with a fluid length to sequent fluid length ratio at the target time being functionally related to a target temperature of the bulb to a sequent target temperature of the sequent bulb ratio at the target time.

When the fluid and the sequent fluid are gases, fluid properties and sequent fluid properties make acoustic imaging well adapted for projecting images of the fluid length and the sequent fluid length outside of the body. Markers 271 and 371 can be included so that the position of the piston 214 relative to the bulbs on an image projected outside of the body can be easily measured. The position of the piston can also be determined by measuring effects on an electric circuit outside of the body.

Other equivalent forms for the thermometers will be obvious hereafter to persons skilled in the art. Therefore this invention is not limited to the particular examples shown and described here.

I claim:

1. Thermometer implants comprising a thermometer body, the thermometer body enclosing a channel and a bulb, the channel being terminated by the bulb at an end, the channel and the bulb containing a fluid, the fluid expanding and contracting along the channel to a fluid length which is functionally related to a target temperature of the bulb at a target time, the thermometer body being adapted to be located in a subject body from where the fluid length is not visible at the target time, and thermometer body properties and fluid properties together making possible measurement of the fluid length outside of the subject body, the thermometer implant further comprising a sequent thermometer body, the sequent thermometer body enclosing a sequent channel and a sequent bulb, the sequent channel being terminated at an end by the sequent bulb, the sequent bulb and the sequent channel containing a sequent fluid, the sequent fluid expanding and contracting along the sequent channel to a sequent thermometer fluid length which is functionally related to a sequent target temperature of the sequent bulb at a sequent target time, the sequent thermometer body being adapted to be located in the subject body from where the sequent fluid is not visible at the sequent target time, and sequent thermometer body properties and sequent fluid properties together making possible measurement of the fluid length outside of the subject body.

2. Thermometer implants comprising a thermometer body, the thermometer body enclosing a channel and a bulb, the channel being terminated by the bulb at an end, the channel and the bulb containing a fluid, the fluid expanding and contracting along the channel to a fluid length which is functionally related to a target temperature of the bulb at a target time, the thermometer body being adapted to be located in a subject body from where the fluid length is not visible at the target time, and thermometer body properties and fluid properties together making possible measurement of the fluid length outside of the subject body, the thermometer implant, and wherein the thermometer body encloses a sequent channel and a sequent bulb, the sequent channel being terminated by the sequent bulb at an end, the sequent bulb and the sequent channel containing a sequent fluid, the sequent fluid expanding and contracting along the sequent channel to a sequent fluid length which is functionally related to a sequent target temperature of the sequent bulb at a sequent target time, the sequent fluid length being not visible at the target time, and sequent fluid properties making possible measurement of the sequent fluid length outside of the subject body.

3. The device of claim 2 wherein the channel and sequent channel form a contiguous channel, the contiguous channel having a movable piston riding in the contiguous channel dividing the fluid from the sequent fluid with a fluid length to sequent fluid length ratio at the target time being functionally related to a target temperature to sequent target temperature ratio at the target time.

4. Thermometer implants comprising a thermometer body, the thermometer body enclosing a channel and a bulb, the channel being terminated by the bulb at an end, the channel and the bulb containing a fluid, the fluid expanding and contracting along the channel to a fluid length which is functionally related to a target temperature of the bulb at a target time, the thermometer body being adapted to be located in a subject body from where the fluid length is not visible at the target time, and thermometer body properties and fluid properties together making possible measurement of the fluid length outside of the subject body, the thermometer implant, and wherein the channel is folded.

5. Thermometer implants comprising a thermometer body, the thermometer body enclosing a channel and a bulb, the channel being terminated by the bulb at an end, the channel and the bulb containing a fluid, the fluid expanding and contracting along the channel to a fluid length which is functionally related to a target temperature of the bulb at a target time, the thermometer body being adapted to be located in a subject body from where the fluid length is not visible at the target time, and thermometer body properties and fluid properties together making possible measurement of the fluid length outside of the subject body, the thermometer implant, the thermometer implant including a trigger mechanism which is remotely activated and which locks the fluid length so that the fluid length does not change after the trigger mechanism is activated.

6. Thermometer implants comprising a thermometer body, the thermometer body enclosing a channel and a bulb, the channel being terminated by the bulb at an end, the channel and the bulb containing a fluid, the fluid expanding and contracting along the channel to a fluid position which is functionally related to a target temperature of the bulb at a target time, the thermometer body being adapted to be located in a subject body from where the fluid position is not visible at the target time, and thermometer body properties and fluid properties together making possible determination of the fluid position outside of the subject body without requiring the use of a physical connection to the device from outside the subject body and wherein the thermometer implant includes at least one marker located on the thermometer body.

7. The device of claim 6 wherein the at least one marker located on the thermometer body is adapted to calibrate a projected image of the fluid.

8. The device of claim 6 further comprising a sequent thermometer body, the sequent thermometer body enclosing a sequent channel and a sequent bulb, the sequent channel being terminated at one end by the sequent bulb, the sequent bulb and the sequent channel containing a sequent fluid, the sequent fluid expanding and contracting along the sequent channel to a sequent thermometer fluid position which is functionally related to a sequent target temperature of the sequent bulb at a sequent target time, the sequent thermometer body being adapted to be located in the subject body from where the sequent fluid is not visible at the sequent target time, and sequent thermometer body properties and sequent fluid properties together making possible determination of the fluid position outside of the subject body.

9. The device of claim 6 wherein the thermometer body encloses a sequent channel and a sequent bulb, the sequent channel being terminated by the sequent bulb at one end, the sequent bulb and the sequent channel containing a sequent fluid, the sequent fluid expanding and contracting along the sequent channel to a sequent fluid position which is functionally related to a sequent target temperature of the sequent bulb at a sequent target time, the sequent fluid position being not visible at the target time, and sequent fluid properties making possible determination of the sequent fluid position outside of the subject body.

10. The device of claim 9 wherein the channel and sequent channel form a contiguous channel, the contiguous channel having a movable piston riding in the contiguous channel dividing the fluid from the sequent fluid with a fluid position to sequent fluid position ratio at the target time being functionally related to a target temperature to sequent target temperature ratio at the target time.

11. The device of claim 6 wherein the channel is folded.

12. The device of claim 6 wherein the subject body is in, and alternatively is intended for use in, a living human.

13. The device of claim 6 further comprising a trigger mechanism which is remotely activated and which locks the fluid position so that the fluid position does not change after the trigger mechanism is activated.

* * * * *